(12) United States Patent
Mishima et al.

(10) Patent No.: US 8,809,609 B2
(45) Date of Patent: Aug. 19, 2014

(54) DEHYDROGENATION CATALYST FOR ALKYL AROMATIC COMPOUNDS EXHIBITING HIGH PERFORMANCE IN THE PRESENCE OF HIGH-CONCENTRATION $CO_2$

(75) Inventors: Yuji Mishima, Toyama (JP); Shinya Hirahara, Toyama (JP); Nobuaki Kodakari, Toyama (JP)

(73) Assignee: Sued-Chemie Catalysts Japan, Inc., Tokyo (JP)

( * ) Notice: Subject to any disclaimer, the term of this patent is extended or adjusted under 35 U.S.C. 154(b) by 55 days.

(21) Appl. No.: 13/128,215

(22) PCT Filed: Nov. 7, 2008

(86) PCT No.: PCT/JP2008/070343
§ 371 (c)(1),
(2), (4) Date: May 6, 2011

(87) PCT Pub. No.: WO2010/052792
PCT Pub. Date: May 14, 2010

(65) Prior Publication Data
US 2011/0213189 A1    Sep. 1, 2011

(51) Int. Cl.
*C07C 5/367* (2006.01)

(52) U.S. Cl.
USPC .......................................... 585/443; 585/444

(58) Field of Classification Search
CPC . C07C 5/367; B01J 2523/13; B01J 2523/842; B01J 2523/23
USPC ................................................ 585/443, 444
See application file for complete search history.

(56) References Cited

U.S. PATENT DOCUMENTS

| | | | |
|---|---|---|---|
| 4,565,898 A | 1/1986 | O'Hara et al. | |
| 2002/0183573 A1 | 12/2002 | Cocco et al. | |
| 2003/0166984 A1 | 9/2003 | Park et al. | |
| 2004/0009871 A1 | 1/2004 | Hu et al. | |
| 2004/0077483 A1 | 4/2004 | O'Brien et al. | |
| 2004/0235652 A1 | 11/2004 | Smith et al. | |
| 2006/0101944 A1 | 5/2006 | Petrini et al. | |
| 2006/0106268 A1 | 5/2006 | Kowaleski | |

FOREIGN PATENT DOCUMENTS

| | | |
|---|---|---|
| CN | 1032119 A | 4/1989 |
| CN | 101165031 B | 8/2010 |
| DE | 60306973 T2 | 1/2007 |
| EP | 1342710 A2 | 9/2003 |
| EP | 1509323 A1 | 3/2005 |
| EP | 1663855 A1 | 6/2006 |
| EP | 1768779 A2 | 4/2007 |
| JP | S64-045320 A | 2/1989 |
| JP | H03-011812 B | 2/1991 |
| JP | H05-038800 B | 6/1993 |
| JP | 2003277299 A | 10/2003 |
| JP | 3881376 B | 2/2007 |
| JP | 2008183492 A | 8/2008 |
| KR | 20030072241 A | 9/2003 |
| KR | 20030072541 A | 9/2003 |
| WO | 9949968 | 10/1999 |
| WO | 03097236 A1 | 11/2003 |
| WO | 2005019099 A1 | 3/2005 |
| WO | 2006012152 A2 | 2/2006 |
| WO | 2006055712 A1 | 5/2006 |
| WO | 2008090974 A1 | 7/2008 |

OTHER PUBLICATIONS

Oil Academy, Petrochemical Process, The Japan Petroleum Institute, 2001, p. 86, Ed.
Takenori Hirano, Changing of Ethyl Benzene Dehydrogenation Catalyst, 1987, Catalyst, vol. 29, No. 8, p. 641.
Akihiko Miyakoshi, Research for Catalyst of Ethyl Benzene Dehydrogenation Reaction, 2006, Petrotech, vol. 29, No. 3, p. 158.
Chinese Office Action, dated Nov. 29, 2012, pp. 1-2.

*Primary Examiner* — Thuan D Dang
(74) *Attorney, Agent, or Firm* — George R. McGuire; Blaine T. Bettinger; Bond Schoeneck & King, PLLC

(57) ABSTRACT

A dehydrogenation catalyst composition for use in preparing an alkenyl aromatic compound by dehydrogenation of an alkyl aromatic compound, a method for preparing the catalyst, and a process for using the catalyst in a dehydrogenation reaction. Carbon dioxide ($CO_2$) is present in the reaction in a molar ratio of 0.015 to 0.20 based on an aromatic compound in a material gas. The catalyst further includes an iron compound, an alkali metal, and about 13 to about 60 wt % of a rare earth element calculated as an oxide.

4 Claims, No Drawings

DEHYDROGENATION CATALYST FOR ALKYL AROMATIC COMPOUNDS EXHIBITING HIGH PERFORMANCE IN THE PRESENCE OF HIGH-CONCENTRATION $CO_2$

CROSS-REFERENCE TO RELATED APPLICATIONS

The present application is the United States national stage filing under 35 U.S.C. 371 of PCT Application Ser. No. PCT/JP2008/070343, filed on Nov. 7, 2008, the entirety of which is relied upon and incorporated herein by reference in its entirety.

BACKGROUND OF THE INVENTION

1. Field of the Invention

The present invention relates to a catalyst for preparing an alkenyl aromatic compound by dehydrogenating an alkyl aromatic compound wherein $CO_2$ is present in a molar ratio of approximately 0.015 to 0.20.

2. Description of the Related Art

Styrene, which is an alkyenyl aromatic compound, is an important industrial material widely used as a material for the production of polystyrene, acrylonitrile butadiene styrene ("ABS") resin or synthetic rubber. Styrene is industrially produced by reacting ethylbenzene under dilute conditions mainly by means of a catalyst having an iron oxide and an alkali metal, in particular potassium, as main components in an insulation type-dehydrogenation reaction which is doubly or triply arranged in series. However, the dehydrogenation reaction of ethylbenzene to the styrene monomer is an equilibrium reaction, and thus the reaction is largely prevented by the generated hydrogen. Also, because the dehydrogenation reaction is endothermic, the temperature decreases as the reaction proceeds, which is disadvantageous with regard to the rate of reaction. For at least these reasons, it is difficult to obtain styrene in a high yield using production equipment in which the above-mentioned dehydrogenation reactors are arranged in series.

As described in "Petrochemical Process," (2001), p 86, Ed. *The Japan Petroleum Institute*; U.S. Pat. No. 4,565,898; and Japan Patent No. H05-38800, it has been proposed that the hydrogen generated from the dehydrogenation reaction of ethylbenzene to the styrene monomer can be selectively oxidized by means of oxygen and thus partially removed, resulting in the equilibrium of the reaction shifting to the product, with the heat of the oxidation reaction compensating the decreasing temperature by the dehydrogenation reaction. However, in such a process, oxygen added in the oxidation step partially reacts with hydrocarbons other than hydrogen to generate $CO_2$. The dehydrogenation catalyst disposed in the downstream oxidation step is generally used as the catalyst having iron oxide and potassium as main components, and as described in *Catalyst* 29:8 pg. 641 (1987) and *Petrotech* 29:3 pg. 158 (2006), $CO_2$ results in a significant decrease in the conversion and selectiveness of the dehydrogenation catalyst. Therefore, this results in an industrial disadvantage.

In yet another improvement of the dehydrogenation catalyst of ethylbenzene, when the reaction in which a conventional preparation process, i.e. a preparation process which comprises diluting ethylbenzene without the oxidation step is carried out under a mild condition such that less $CO_2$ is generated, a variety of improved process are proposed, for example, a modification of the composition in catalyst as described in Japan Patent Nos. JP-A H03-11812 and JP-A S64-45320, as well as a variation in a pore size distribution of a material as described in Japan Patent No. 3881376. However, it has not previously been proposed to use the high-yield dehydrogenation catalyst under a specific reaction condition, for example, in the presence of highly-concentrated $CO_2$ which is employed in the dehydrogenation step disposed in the downstream oxidation step as above-mentioned.

Description Of the Related Art Section Disclaimer: To the extent that specific publications are discussed above in this Description of the Related Art Section, these discussions should not be taken as an admission that the discussed publications (for example, published patents) are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section, they are all hereby incorporated by reference into this document in their respective entireties.

BRIEF SUMMARY OF THE INVENTION

Problems to be Resolved by the Invention

To solve the above-mentioned disadvantages in the related art, the present invention relates to a catalyst for preparing an alkenyl aromatic compound by dehydrogenating an alkyl aromatic compound, and therefore it is the object of the present invention to provide a high performance dehydrogenation catalyst of an alkyl aromatic compound in the presence of a highly concentrated $CO_2$, a process for preparation thereof, and a process for dehydrogenation using it.

Means of Solving the Problems

We have diligently investigated and found that the catalyst which comprises about 13 to about 60% by weight of the rare earth element calculated as the oxide weight in the alkali metal and iron compound-containing dehydrogenation catalyst has a very high yield of the alkenyl aromatic compound under the condition of highly concentrated $CO_2$.

In accordance with the foregoing objects and advantages, the present invention provides a dehydrogenation catalyst composition for use in preparing an alkenyl aromatic compound by dehydrogenating of an alkyl aromatic compound. The catalyst comprises at least steam, carbon dioxide which is present in a molar ratio from about 0.015 to about 0.20 based on an aromatic compound in a material gas, which comprises from about 30 to about 86 wt % of an iron compound calculated as $Fe_2O_3$, from about 1 to about 50 wt % of an alkali metal calculated as an alkali metal oxide, and about 13 to about 60 wt % of a rare earth element calculated as an oxide, wherein all weight percents are based on the total weight of the catalyst. In a preferred embodiment, the alkyl aromatic compound in the reaction is ethylbenzene, and the alkenyl aromatic compound is styrene. Further, in the preferred embodiment the iron compound is iron oxide and comprises potassium with the formula $K_2O\cdot(Fe_2O_3)_n$ in which n is between 1 and 11.

The alkali metal is preferably a sodium compound, a potassium compound, or a potassium carbonate, and the rare earth element is lanthanum or cerium.

The present invention further provides the above dehydrogenation catalyst, but also includes about 0.2 to about 10% wt % of an alkali earth metal calculated as an alkali earth metal oxide, and about 0.2 to about 10% by weight of a transition metal compound calculated as a transition metal oxide compound, with all weight percents based on the total weight of the catalyst. In a preferred embodiment, the transition metal compound is a molybdenum compound calculated as $MoO_3$, or a tungsten compound calculated as $WO_3$.

The dehydrogenation catalyst can further comprise about 1 to 200 ppm of a noble metal, where the noble metal is palladium, platinum, iridium, rhodium, and/or ruthenium.

The present invention further provides a method for preparation of a sintered dehydrogenation catalyst. The method comprises the steps of: (i) mixing any of the dehydrogenation catalyst compositions described, discussed, or suggested herein with water to prepare extrudable mixture; (ii) molding the extrudable mixture to make a pellet; (iii) drying the pellet; and (iv) sintering the pellet.

The present invention also provides a dehydrogenation process. The dehydrogenation process comprises the steps of: (i) contacting any of the dehydrogenation catalyst compositions described, discussed, or suggested herein with a reaction gas, where the reaction gas comprises steam, an alkyl aromatic compound, and carbon dioxide where the carbon dioxide is present in a molar ratio from about 0.015 to about 0.20 based on all aromatic molecules in the reaction; and (ii) producing an alkenyl aromatic compound.

DETAILED DESCRIPTION OF THE INVENTION

According to the present invention is provided a catalyst for preparing an alkenyl aromatic compound by dehydrogenating an alkyl aromatic compound wherein $CO_2$ is present in a molar ratio of approximately 0.015 to 0.20 and further wherein the expected decrease in yield caused by carbon dioxide is largely avoided, where the catalyst comprises about 13% to about 60% by weight of a rare earth element calculated as the oxide weight in the alkali metal and iron compound-containing dehydrogenation catalyst. The present invention is explained in more detail below.

In the dehydrogenation reaction of a alkyl aromatic compound, the dehydrogenation reaction condition in which much $CO_2$ is contained means that $CO_2$ in the system is present in a molar ration of 0.015 to 0.20 based on a total flow rate of all aromatic molecules such as an unreacted alkyl aromatic compound and the alkenyl aromatic compound in a product. $CO_2$ contained in the reaction is produced by a secondary reaction in the step for selectively oxidizing hydrogen generated from the dehydrogenation reaction with the oxidation catalyst.

More particular, in a process consisting of the following steps: (i) the oxidation step for mixing the material gas consisting of a mixture of the unreacted alkyl aromatic compound, the alkenyl aromatic compound, hydrogen, and the steam with an oxygen-containing gas to oxidatively react hydrogen in the presence of an oxidation catalyst, and (ii) the dehydrogenation step for dehydrogenating a reaction gas containing the $CO_2$ by-product by reacting the unreacted alkyl aromatic compound, the alkenyl aromatic compound, hydrogen, the steam, and a part of the alkyl aromatic compound eluting from the oxidation step with oxygen by means of the dehydrogenation catalyst to produce the alkenyl aromatic compound, the dehydrogenation catalyst is used in the dehydrogenation step in which the concentration of $CO_2$ disposed in the downstream oxidation step is enhanced. The concentration of $CO_2$ in the reaction gas in the downstream oxidation step is in a molar ratio of 0.015 to 0.20 based on a total flow rate of all aromatic molecules contained in the material gas comprising an unreacted alkyl aromatic compound and the alkenyl aromatic compound. In addition, the oxidation step is well-known, and the product stream consisting of the unreacted hydrocarbon, the dehydrogenated hydrocarbon, the steam, and hydrogen after a conventional dehydrogenation step is subjected to the selective oxidation in the contacting the oxygen-containing gas with an oxidized catalytic bed. A catalyst used in the dehydrogenation step and the oxidation step prior to the reaction process which utilizes the catalyst according to the invention is well-known. For example, the dehydrogenation catalyst used in the prior process consisted of an alkali metal-promoting iron compound, and the oxidation catalyst is any one of catalysts which selectively oxidize hydrogen and is consisted of the noble metal in the VIII group of the periodic table, such as platinum, on an α-alumina.

The dehydrogenation catalyst of the alkyl aromatic compound according to the present invention is useful as the dehydrogenation catalyst by means of which the alkenyl aromatic compound is generated by contacting the alkyl aromatic compound with the steam, in particular, is useful for promoting the dehydrogenation of ethylbenzene if contacting the ethylbenzene with the steam is carried out to produce styrene, and is adequately useful for the dehydrogenation reaction step in which the concentration of $CO_2$ is enhanced after the oxidation step. The process for dehydrogenation using the catalyst according to the invention is carried out as a successive operation utilizing a fixed bed, and the fixed bed may consist of one stage or be a series of stages which consist of the same or different catalysts in one reaction or two more reactions. Then, other types of reactions and the reaction form also can be used for the dehydrogenation process.

In the process for dehydrogenation using the catalyst according to the present invention, a mixing ratio of the steam to a total flow rate of the alkyl aromatic compound and the alkenyl aromatic compound contained in the material gas after the oxidation step is not limited, however, it is usually from 3 to 15 of the molar ratio, preferably 5 to 13. The reaction temperature of a catalyst layer in which the gaseous material with the composition is contacted with the catalyst layer is usually 500° C. or, more preferably, 530° C. or more. Also, the reaction pressure may be 0.1 to 3 ATM. Preferably, the supply rate of the alkyl aromatic compound is 0.1 to 10 $h^{-1}$ in Liquid Hourly Space Velocity ("LHSV").

In the catalyst according to the present invention which is used for the dehydrogenation step of the alkyl aromatic compound in the reaction system in which much $CO_2$ is contained, it is important that the rare earth element comprise about 13% to about 60% by weight, as the oxide weight. With more of the rare earth element, the conversion of the alkyl aromatic compound is higher. Also, if the content of the rare earth element is less than 13% by weight, the industrially useful conversion cannot be obtained. Similarly, if it is more than 60% by weight, the conversion is higher but it is not practical due to the expensive of the catalyst material. Preferably, the rare earth element for the catalyst is, in particular, cerium or lanthanum, both of which are basic.

Also, in the composition of the catalyst according to the present invention, the composition other than the rare earth element as mentioned above may be a general composition in which the catalyst comprises iron oxide and an alkali metal.

The iron material for the present invention is basically red, yellow, brown, and black iron oxides in a variety of forms. It is added as the red iron oxide $Fe_2O_3$ or the yellow iron oxide $Fe_2O_3.H_2O$, but it is not necessarily so, and any iron oxide precursor—such as goethite or a basic sodium carbonate which can convert to the iron oxide during sintering of the catalyst—can be used. Ferrite can also be used as the iron compound. Preferably, potassium ferrite can be used.

The alkali metal is selected from the group consisting of lithium, sodium, potassium, rubidium, and cesium. Also, in addition to the iron oxide-alkali metal, other elements may be comprised in an amount that has already been proposed. For example, to improve the selectiveness, the alkali earth metal containing molybdenum, tungsten, barium, francium, and radium, or the noble metal selected from the group consisting of palladium, platinum, iridium, rhodium, and ruthenium may be contained.

In one embodiment of the composition of the catalyst according to the present invention, it is possible to comprise: (i) about 30% to about 86% by weight of the iron compound $Fe_2O_3$; (ii) about 1% to about 50% by weight of an alkali metal calculated as an alkali metal oxide; and (iii) about 13% to about 60% by weight of a rare earth element calculated as an oxide.

Moreover, a suitable embodiment of the composition of the catalyst according to the present invention is listed as follows:

| Compound | Composition |
| --- | --- |
| $Fe_2O_3$ | 30 to 85.5% by weight |
| Alkali metal (in the oxide weight) | 1 to 50% by weight |
| Alkali earth metal (in the oxide weight) | 0.2 to 10% by weight |
| $MoO_3$ or $WO_3$ | 0.2 to 10% by weight |
| Rare earth element (in the oxide weight) | 13 to 60% by weight |
| Noble metal | 1 to 200 ppm |

The catalyst according to the present invention is finally sintered in the range of 500 to 1100° C., and thus any promoter compounds can be used if the compounds can be decomposed by thermally treating them. Usually, in consideration of the ease of access and economic efficiency, it is preferable to use a carbonate or a hydroxide as the alkali metal, the alkali earth metal, or the rare earth element. Preference is given to use of p-ammonium molybdate and p-ammonium tungstate or molybdenum oxide or tungsten oxide as molybdenum or tungsten.

The catalyst according to the present invention can be prepared using usual methods. For example, it is prepared by mixing an essential component as mentioned above with an optional component and sintering the generated mixture. Preferably, the material for the catalyst is moistly kneaded. In this case, it is necessary for an amount of the added water in the kneading to adapt to the amount in the subsequent extruding. The amount, depending on the material used, is usually 2% to 50% by weight, and, after sufficiently kneading it, it is extruded and then sintered to obtain a dehydrogenation catalyst. When drying, it is sufficient to remove free water possessed in the extrusion, and it is carried out at the temperature of 60 to 200° C., preferably 70 to 180° C. On the other hand, the sintering is carried out to thermally decompose each catalyst precursors possessed in a dry substance, to improve the physical stability of the catalyst pellet and to improve its performance, and is carried out at the temperature of 500 to 1100° C., preferably 500 to 900° C.

If the catalyst according to the present invention can be used as a typical fixed-bed catalyst, it has any shape, for example, round, cylindrical, macaroni, and bulk.

The present invention is explained in detail in the Examples and Comparative Examples mentioned below. However, it should be noted that the invention is not limited to these Examples and Comparative Examples. Unless otherwise stated, part and % is based on the weight.

Example 1

In Example 1, 527.3 g of red iron oxide (hematite crystal structure), 331.6 g of potassium carbonate, and 376.6 g of cerium carbonate hydrate were weighed into a kneading machine and deionized water was added dropwise with stifling to form a paste. The mixed paste obtained was sintered at 900° C. for 2 hours, milled, and then granulated by means of a sieve having an opening size of 2.36 mm and a sieve having an opening size of 1.40 mm. This resulted in a dehydrogenation catalyst comprising 56.0% of iron oxide calculated as $Fe_2O_3$, 24.0% of potassium calculated as $K_2O$, and 20.0% of cerium calculated as $CeO_2$. A reaction test was carried out with using the dehydrogenation catalyst obtained under the reaction condition described in Table 1.

TABLE 1

| | |
| --- | --- |
| Amount of catalyst | 20 cc |
| Liquid Hourly Space Velocity (LHSV) of material ethylbenzene | 5.0 h$^{-1}$ |
| (diluted H$_2$O flow rate) ÷ (material ethylbenzene flow rate) | 1.60 wt/wt (ratio by weight) |
| reaction pressure | 61 kPa (absolute pressure) |
| reaction temperature | 600° C. |

After confirming conversion of the reactant calculated by the following equation was stable, addition of $CO_2$ gas into the above-described reaction condition was started at a flow rate corresponding to ($CO_2$ flow rate)÷(material ethylbenzene flow rate)=0.03 after 72 hours from the start of flowing of ethylbenzene. The conversion was measured after 23 hours from the start of flowing of $CO_2$:[conversion (mole %)=(supplied ethylbenzene (mole)−discharged ethylbenzene (mole))÷supplied ethylbenzene (mole)×100]. Then, the flow rate of the added $CO_2$ was increased to a flow rate corresponding to: [($CO_2$ flow rate)÷(material ethylbenzene flow rate)= 0.06 after 24 hours from the start of flowing of $CO_2$]. The conversion was measured after 47 hours from the start of flowing of $CO_2$. In addition, the flow rate of the added $CO_2$ was increased to a flow rate corresponding to: [($CO_2$ flow rate)÷(material ethylbenzene flow rate)=0.13 after 48 hours from the start of flowing of $CO_2$]. The conversion was measured after 71 hours from the start of flowing of $CO_2$. The obtained results are shown in Table 2.

Comparative Example 1

Ethylbenzene conversions at each concentration under flowing of $CO_2$ were measured in the same manner as in Example 1 except for preparing a catalyst comprising 76.0% of iron oxide calculated as $Fe_2O_3$ and 24.0% of potassium calculated as $K_2O$ by using 715.6 g of red iron oxide (hematite crystal structure) and 331.6 g of potassium carbonate. The obtained results are shown in Table 2.

Example 2

In this Example, 697.3 g of red iron oxide (hematite crystal structure), 166.5 g of potassium carbonate and 405.4 g of cerium carbonate hydrate were weighed into a kneading machine and deionized water was added dropwise with stifling to form a paste. The mixed paste obtained was sintered at 900° C. for 2 hours, milled, and then glanulated by means of a sieve having an opening size of 2.36 mm and a sieve having an opening size of 1.40 mm. This gave a dehydrogenation catalyst comprising 68.8% of iron oxide calculated as $Fe_2O_3$, 11.2% of potassium calculated as $K_2O$ and 20.0% of cerium calculated as $CeO_2$. A reaction test was carried out with using the dehydrogenation catalyst obtained under the reaction conditions shown in Table 1.

After confirming that a conversion had been stable, an addition of $CO_2$ gas into the above-described reaction condition was started at a flow rate corresponding to ($CO_2$ flow rate)÷(material ethylbenzene flow rate)=0.03 after 72 hours from the start of flowing of ethylbenzene. The conversion was measured after 23 hours from the start of flowing of $CO_2$. Table 3 shows conversions at the each concentration under flowing of $CO_2$.

Example 3

Conversions at the each concentration under flowing of $CO_2$ were measured in the same manner as in Example 2 except for preparing a catalyst comprising 68.8% of iron oxide calculated as $Fe_2O_3$, 11.2% of potassium calculated as $K_2O$, 10.0% of cerium calculated as $CeO_2$ and 10.0% of lanthanum calculated as $La_2O_3$ by using 697.3 g of red iron oxide (hematite crystal structure), 166.5 g of potassium carbonate, 202.7 g of cerium carbonate hydrate and 187.3 g of lanthanum carbonate octahydrate. The obtained results are shown in Table 3.

Comparative Example 2

Conversions at the each concentration under flowing of $CO_2$ were measured in the same manner as in Example 2 except for preparing a catalyst comprising 88.8% of iron oxide calculated as $Fe_2O_3$ and 11.2% of potassium calculated as $K_2O$ by using 900.0 g of red iron oxide (hematite crystal structure) and 166.5 g of potassium carbonate. The obtained results are shown in Table 3.

Example 4

Conversions at the each concentration under flowing of $CO_2$ were measured in the same manner as in Example 2 except for preparing a catalyst comprising 48.8% of iron oxide calculated as $Fe_2O_3$, 11.2% of potassium calculated as $K_2O$ and 40.0% of cerium calculated as $CeO_2$ by using 494.6 g of red iron oxide (hematite crystal structure), 166.5 g of potassium carbonate and 810.8 g of cerium carbonate hydrate. The obtained results are shown in Table 3.

Example 5

Conversions at the each concentration under flowing of $CO_2$ were measured in the same manner as in Example 2 except for preparing a catalyst comprising 75.8% of iron oxide calculated as $Fe_2O_3$, 11.2% of potassium calculated as $K_2O$ and 13.0% of cerium calculated as $CeO_2$ by using 768.0 g of red iron oxide (hematite crystal structure), 166.5 g of potassium carbonate and 263.4 g of cerium carbonate hydrate. The obtained results are shown in Table 3.

Comparative Example 3

Conversions at the each concentration under flowing of $CO_2$ were measured in the same manner as in Example 2 except for preparing a catalyst comprising 83.8% of iron oxide calculated as $Fe_2O_3$, 11.2% of potassium calculated as $K_2O$ and 5.0% of cerium calculated as $CeO_2$ by using 849.1 g of red iron oxide (hematite crystal structure), 166.5 g of potassium carbonate and 101.3 g of cerium carbonate hydrate. The obtained results are shown in Table 3.

Example 6

Conversions at the each concentration under flowing of $CO_2$ were measured in the same manner as in Example 2 except for preparing a catalyst comprising 67.8% of iron oxide calculated as $Fe_2O_3$, 11.2% of potassium calculated as $K_2O$, 20.0% of cerium calculated as $CeO_2$, 0.5% of calcium calculated as CaO and 0.5% of molybdenum calculated as $MoO_3$ by using 687.1 g of red iron oxide (hematite crystal structure), 166.5 g of potassium carbonate, 405.4 g of cerium carbonate hydrate, 6.7 g of calcium hydroxide and 5.1 g of molybdenum trioxide. The obtained results are shown in Table 4.

Comparative Example 4

Conversions at the each concentration under flowing of $CO_2$ were measured in the same manner as in Example 2 except for preparing a catalyst comprising 87.8% of iron oxide calculated as $Fe_2O_3$, 11.2% of potassium calculated as $K_2O$, 0.5% of calcium calculated as CaO and 0.5% of molybdenum calculated as $MoO_3$ by using 889.9 g of red iron oxide (hematite crystal structure), 166.5 g of potassium carbonate, 6.7 g of calcium hydroxide and 5.1 g of molybdenum trioxide. The obtained results are shown in Table 4.

Example 7

Conversions at the each concentration under flowing of $CO_2$ were measured in the same manner as in Example 2 except for preparing a catalyst comprising 67.8% of iron oxide calculated as $Fe_2O_3$, 11.2% of potassium calculated as $K_2O$, 20.0% of cerium calculated as $CeO_2$, 0.5% of calcium calculated as CaO, 0.5% of molybdenum calculated as $MoO_3$ and 100 ppm of palladium metal by using 687.1 g of red iron oxide (hematite crystal structure), 166.5 g of potassium carbonate, 405.4 g of cerium carbonate hydrate, 6.7 g of calcium hydroxide, 5.1 g of molybdenum trioxide and palladium nitrate solution. The obtained results are shown in Table 4.

TABLE 2

| | Composition | | | $CO_2$ ÷ ethyl-benzene ratio | Ethylbenzene conversion |
|---|---|---|---|---|---|
| Example | $Fe_2O_3$ | $K_2O$ | $CeO_2$ | (mole/mole) | (mole %) |
| Example 1 | 56.0% | 24.0% | 20.0% | 0.03 | 38.3 |
| | | | | 0.06 | 28.2 |
| | | | | 0.13 | 18.6 |
| Comparative Example 1 | 76.0% | 24.0% | | 0.03 | 10.1 |
| | | | | 0.06 | 6.7 |
| | | | | 0.13 | 4.8 |

TABLE 3

| | Composition | | | | Ethylbenzene conversion |
|---|---|---|---|---|---|
| Example | $Fe_2O_3$ | $K_2O$ | $CeO_2$ | $La_2O_3$ | (mole %) |
| Example 2 | 68.8% | 11.2% | 20.0% | | 53.5 |
| Example 3 | 68.8% | 11.2% | 10.0% | 10.0% | 36.6 |
| Comparative Example 2 | 88.8% | 11.2% | | | 26.5 |
| Example 4 | 48.8% | 11.2% | 40.0% | | 68.1 |

TABLE 3-continued

| Example | Composition | | | | Ethylbenzene conversion (mole %) |
|---|---|---|---|---|---|
| | $Fe_2O_3$ | $K_2O$ | $CeO_2$ | $La_2O_3$ | |
| Example 5 | 75.8% | 11.2% | 13.0% | | 49.8 |
| Comparative Example 3 | 83.8% | 11.2% | 5.0% | | 35.5 |

TABLE 4

| Example | Composition | | | | | | Ethylbenzene conversion (mole %) |
|---|---|---|---|---|---|---|---|
| | $Fe_2O_3$ | $K_2O$ | $CeO_2$ | CaO | $MoO_3$ | Pd | |
| Example 6 | 67.8% | 11.2% | 20.0% | 0.5% | 0.5% | | 41.2 |
| Comparative Example 4 | 87.8% | 11.2% | | 0.5% | 0.5% | | 12.0 |
| Example 7 | 67.8% | 11.2% | 20.0% | 0.5% | 0.5% | 100 ppm | 48.2 |

The above-mentioned Examples and Comparative Examples show that the catalyst according to the present invention can achieve a significantly high yield under a concentration high of carbon dioxide.

INDUSTRIAL APPLICABILITY

The dehydrogenation catalyst of the present invention can produce an alkenyl aromatic compound in high yield under high carbon dioxide concentration in which the concentration of $CO_2$ is present in a molar ratio of 0.015 to 0.20 based on all aromatic molecules including the alkyl aromatics in the material gas without reduction of yield owing to $CO_2$ in a conventional method. Therefore, the dehydrogenation catalyst of the present invention, the process for preparing it, and the dehydrogenating process using it contribute greatly to an optimum production system of alkenyl aromatics.

Although the present invention has been described in connection with a preferred embodiment, it should be understood that modifications, alterations, and additions can be made to the invention without departing from the scope of the invention as defined by the claims.

What is claimed is:

1. A method for dehydrogenation of an alkyl aromatic compound, comprising the steps of:
mixing a first gas comprising hydrogen, steam, and the alkyl aromatic compound with a second gas comprising oxygen to form a gas mixture, wherein at least some of said hydrogen is oxidized and carbon dioxide is produced; and
contacting said gas mixture with a reaction gas comprising a dehydrogenation catalyst to produce an alkenyl aromatic compound, wherein said reaction gas comprises steam and carbon dioxide, said carbon dioxide being present in a molar ratio from about 0.015 to about 0.20 based on all aromatic molecules in the reaction, and wherein said dehydrogenation catalyst comprises from about 30 to about 86 wt. % of an iron compound calculated as $Fe_2O_3$, from about 1 to about 50 wt. % of an alkali metal calculated as an alkali metal oxide, and about 13 to about 60 wt. % of a rare earth element calculated as an oxide, wherein all weight percents are based on the total weight of the catalyst.

2. A dehydrogenation process, comprising:
contacting a dehydrogenation catalyst with a reaction gas, wherein said reaction gas comprises steam, an alkyl aromatic compound, and carbon dioxide, said carbon dioxide being present in a molar ratio from about 0.015 to about 0.20 based on all aromatic molecules in the reaction, and wherein said dehydrogenation catalyst comprises from about 30 to about 86 wt % of an iron compound calculated as $Fe_2O_3$, from about 1 to about 50 wt % of an alkali metal calculated as an alkali metal oxide, and about 13 to about 60 wt % of a rare earth element calculated as an oxide, wherein all weight percent are based on the total weight of the catalyst; and
producing an alkenyl aromatic compound.

3. A dehydrogenation process, comprising:
contacting a dehydrogenation catalyst with a reaction gas, wherein said reaction gas comprises steam, an alkyl aromatic compound, and carbon dioxide, said carbon dioxide being present in a molar ratio from about 0.015 to about 0.20 based on all aromatic molecules in the reaction, and wherein said dehydrogenation catalyst comprises from about 30 to about 86 wt % of an iron compound calculated as $Fe_2O_3$, from about 1 to about 50 wt % of an alkali metal calculated as an alkali metal oxide, about 13 to about 60 wt % of a rare earth element calculated as an oxide, about 0.2 to about 10% wt % of an alkali earth metal calculated as an alkali earth metal oxide, and about 0.2 to about 10% by weight of a transition metal compound calculated as a transition metal oxide compound, wherein all weight percent are based on the total weight of the catalyst; and
producing an alkenyl aromatic compound.

4. A dehydrogenation process, comprising:
contacting a dehydrogenation catalyst with a reaction gas, wherein said reaction gas comprises steam, an alkyl aromatic compound, and carbon dioxide, said carbon dioxide being present in a molar ratio from about 0.015 to about 0.20 based on all aromatic molecules in the reaction, and wherein said dehydrogenation catalyst comprises from about 30 to about 86 wt % of an iron compound calculated as $Fe_2O_3$, from about 1 to about 50 wt % of an alkali metal calculated as an alkali metal oxide, about 13 to about 60 wt % of a rare earth element calculated as an oxide, about 0.2 to about 10% wt % of an alkali earth metal calculated as an alkali earth metal oxide, about 0.2 to about 10% by weight of a transition metal compound calculated as a transition metal oxide compound, and about 1 to 200 ppm of a noble metal, wherein all weight percent are based on the total weight of the catalyst; and
producing an alkenyl aromatic compound.

* * * * *